United States Patent [19]

Bethkenhagen et al.

[11] 4,280,509

[45] Jul. 28, 1981

[54] VALVED BLOOD SAMPLING DEVICE

[76] Inventors: Jürgen Bethkenhagen, Heideweg 15, 5223 Nümbrecht; Dieter Kolpe, Rosenfeldstrasse 1, 5276 Wiehl 1, both of Fed. Rep. of Germany

[21] Appl. No.: 956,925

[22] Filed: Nov. 2, 1978

[30] Foreign Application Priority Data

Nov. 11, 1977 [DE] Fed. Rep. of Germany ....... 2750454

[51] Int. Cl.³ .............................................. A61B 5/14
[52] U.S. Cl. ..................... 128/766; 128/764
[58] Field of Search .......................................... 128/766

[56] References Cited

U.S. PATENT DOCUMENTS

| 2,832,344 | 4/1958 | Davidson | 128/766 |
| 3,304,934 | 2/1967 | Bautista | 128/766 |
| 3,491,748 | 1/1970 | Pate | 128/766 |
| 3,616,789 | 11/1971 | Grabhorn | 128/766 X |
| 3,838,843 | 10/1974 | Bernhard | 128/766 |
| 4,106,497 | 8/1978 | Percarpio | 128/766 |

FOREIGN PATENT DOCUMENTS 1586087  2/1970  France ................... 128/766

*Primary Examiner*—Kyle L. Howell
*Attorney, Agent, or Firm*—Browdy and Neimark

[57] ABSTRACT

A cannula for blood extraction with a controllable flow includes an injection cannula and a discharge cannula interconnected by a flexible tube wherein the tube is capable of being squeezed tight between the cannulae by a mechanism which applies pressure to the exterior of the flexible tube, the pressure applying mechanism and the tube serving as a valve between the cannulae.

2 Claims, 3 Drawing Figures

VALVED BLOOD SAMPLING DEVICE

This invention relates to a cannula for blood extraction and provided with a controllable flow, the cannula being applicable for human and animal usage.

With such cannulae, a clean and infection-free extraction of blood from the vein or artery should be insured. When during blood extraction the extraction device, for instance a syringe or a tubule, must be exchanged, it is required to provide a closable valve between the cannula and the extraction device.

With this requirement, the invention is based on the problem of providing a cannula for blood extraction in which the flow is able to be controlled cleanly and infection-free upon a change of the extraction device.

As a technical solution of this problem, it is proposed to connect an injection cannula and a discharge cannula by a flexible tube and to arrange the tube between the cannulae so as to be squeezable in a flow-obstructing manner. The injection cannula is pointed at its free end in the conventional fashion in order to permit the injection thereof into the vein or artery. The discharge cannula on the one hand serves the purpose of passing the blood flowing therefrom in a free flow into a receiving tubule. On the other hand, the discharge cannula may also be pointed at its free end in order to puncture a soft-resilient plug closing the receiving tubule.

Furthermore, it is proposed to install the injection and discharge cannulae as well as the tube in a housing provided with a resilient lever for squeezing tight the tube. To this end, the arrangement and the attachment of the lever in and at the housing may be provided in such a way that the lever is lifted off the tube by the upper rim of a discharge vessel pushed into the housing and thereby the previously shut-off passage is opened.

The advantages obtainable by the invention reside in the fact that the flow of the blood during blood extraction may be interrupted as often as desired, without the injection cannula having to be retracted from the vein or artery. Also, by the valve including the flexible tube and the lever, a dripping or after-flowing of the blood is prevented, which is of great significance for a clean and infection-free blood extraction system.

After effecting blood extraction, the injection cannula is retracted from the vein or artery, and the valve with the housing is discarded. The embodiment of the valve inclusive the housing is so simple that it is able to be produced as a cheap mass product.

Further details and advantages of the subject matter of this invention result from the description of the accompanying drawing to follow, in which a preferred embodiment of a cannula formed according to the invention has been illustrated semi-diagrammatically. In the drawing.

Figure 1:
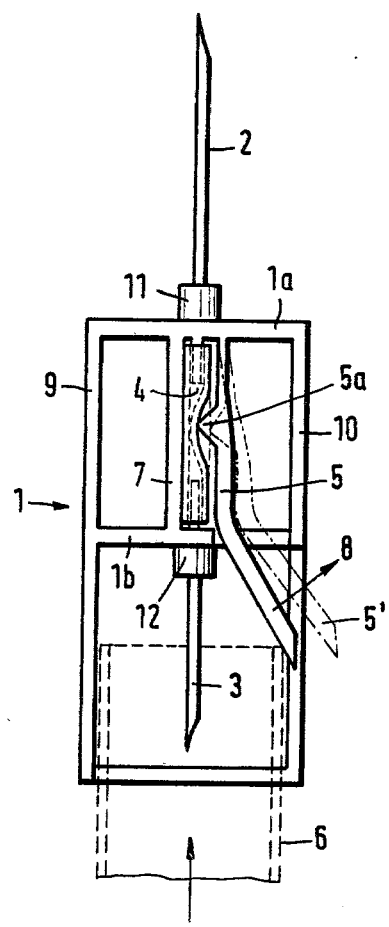
FIG. 1 is a cannula in a front-elevational view.
Figure 2:
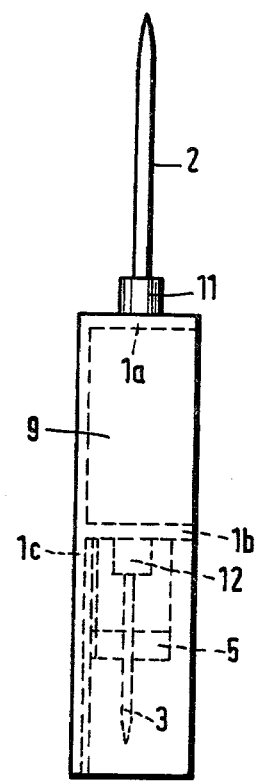
FIG. 2 is the cannula of FIG. 1 in a side-elevational view.

In a housing 1 of plastic, an injection cannula 2 is inserted at one face 1a. Generally midway of the housing 1, parallel to the face 1a, there is an intermediate wall 1b which receives a discharge cannula 3. The two ends of the injection cannula 2 and of the discharge cannula 3 facing each other are interconnected by a flexible tube 4. From the inside surface of the face 1a, a lever 5 projects into the interior of the housing, said lever carrying a projection 5a facing the tube generally at the level of the middle of the tube 4. In the relieved or rest position of the lever 5, the projection 5a squeezes shut the tube 4 which is supported by a web 7 connecting the face 1a to the intermediate wall 1b.

The lever 5 is turned outwardly generally at the level of the intermediate wall 1b and extends through an aperture in the intermediate wall 1b to the side wall of the housing 1 which is provided with a recess there, also. The arrangement is such that upon pushing in a tubule 6 (illustrated in FIG. 1 phantom) the upper rim of this tubule strikes upon the free end of the lever 5 and deflects it outwardly in counteraction to its resiliency in direction of the arrow 8 upon being pushed in further. In FIG. 1, the moment has been illustrated in which the upper rim of the tubule 6 just strikes upon the lever. Upon further pushing upwardly the tubule 6, the lever is brought into the position 5' (shown in phantom). In doing so, the projection 5a at the upper end of the lever releases the wall of the tube 4, and thereby, the flow through the tube is likewise released.

When upon removal of the desired quantity of blood the tubule 6 is retracted from the housing 1 again downwardly, the lever 5 springs back into its position illustrated in full lines, squeezes tight the tube 4 with its projection 5a and thus closes the valve.

Figure 3:
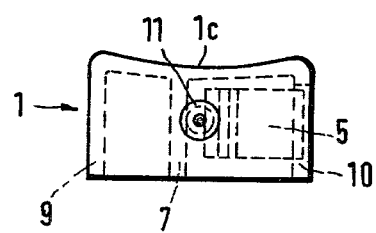
FIG. 3 is the cannula of FIGS. 1 and 2 in a plan view.

The rearward wall 1c of the housing 1 which is integrally connected to the sidewalls 9 and 10, the face 1a, the intermediate wall 1b and the web 7, is formed slightly concave, as will be noted from FIG. 3. The front side of the housing is on the other hand open in order to be able to observe the position of the lever and the flow of the blood.

For receiving the injection cannula 2, a cylindrical projection 11 projects from the face 1a, in the longitudinal bore of which projection 11 the injection cannula 2 is firmly inserted.

In a similar fashion, the intermediate wall 1b at the bottom side carries a cylindrical projection 12 in the longitudinal bore of which the discharge cannula 3 is inserted.

What is claimed is:

1. A device for the extraction of blood with a controllable flow, comprising a housing, an injection cannulae having a first end disposed within said housing, said injection cannulae having a pointed end extending from said housing, a discharge cannulae disposed inside said housing, a flexible tube connecting said discharge cannulae with the first end of said injection cannulae, and a resilient lever disposed in said housing and biased to squeeze closed said flexible tube when in its normal position but capable of releasing said tube upon being tilted away from its normal position, wherein said lever is so positioned that it is forced from its normal position by a tubular container when the tubular container is pushed into said housing.

2. A device for the extraction of blood with a controllable flow, comprising an injection cannula having a first end and a second end, said second end of said injection cannula being pointed; a flexible tube having a first end and a second end, the first end of said flexible tube being connected to the first end of said injection cannula; a discharge cannula having a first end and a second end, the second end of said discharge cannula being connected to the second end of said flexible tube; biased closing means to close said flexible tube by applying pressure to the exterior thereof, said closing means being biased in the closed position so that said flexible tube is normally squeezed closed, and said closing means including an elongated member; and guide means for receiving a tubular container for discharge of blood into the tubular container through the first end of said discharge cannula, said guide means being so positioned in relation to said closing means that insertion of the tubular container into said guide means drives said elongated member of said closing means from its normal position and opens said flexible tube.

* * * * *